United States Patent [19]

Barkhoudarian

[11] Patent Number: 4,567,769
[45] Date of Patent: Feb. 4, 1986

[54] CONTACT-FREE ULTRASONIC TRANSDUCTION FOR FLAW AND ACOUSTIC DISCONTINUITY DETECTION

[75] Inventor: Sarkis Barkhoudarian, Canoga Park, Calif.

[73] Assignee: Rockwell International Corporation, El Segundo, Calif.

[21] Appl. No.: 587,713

[22] Filed: Mar. 8, 1984

[51] Int. Cl.$^4$ ............................................. G01N 29/00
[52] U.S. Cl. ........................................ 73/643; 73/655; 350/96.24; 374/5
[58] Field of Search ...................... 73/643, 655; 374/5; 350/96.24, 358

[56] References Cited

U.S. PATENT DOCUMENTS

| | | | |
|---|---|---|---|
| 4,046,477 | 9/1977 | Kaule | 73/643 |
| 4,144,767 | 3/1979 | Kaule et al. | 73/643 |
| 4,338,822 | 7/1982 | Yamaguchi et al. | 73/643 |
| 4,379,409 | 4/1983 | Prembsch et al. | 73/643 |
| 4,484,820 | 11/1984 | Rosencwaig | 73/643 |

*Primary Examiner*—Howard A. Birmiel
*Attorney, Agent, or Firm*—H. Fredrick Hamann; Harry B. Field; Lawrence N. Ginsberg

[57] ABSTRACT

A system for the examination of a test object for internal flaws (or acoustic discontinuities such as solid-to-gas or solid-to-liquid interfaces) by means of ultrasonic waves. The ultrasonic waves 18 are induced in the object 16 by projecting at least one intense, pulsed laser beam 13 on the object 16 and scanning the beam 18 along the object 16. Another laser beam 23 is projected on the object 16, either opposite the first beam 14 or on the same side adjacent to the first beam 14, so that is reacts with and is frequency-modulated by the ultrasonic wave. The reflected, frequency-modulated beam 24 is fed to an optical heterodyning means 26 which passes through only an optical beam 28 modulated with the ultrasonic frequency to a photodetector 30. A flaw 36 (or acoustic discontinuities such as solid-to-gas or solid-to-liquid interfaces) in the test object 16 results either in a decrease or an increase in the output of the photodetector 30, depending on whether the detection laser beam 23 is on the opposite or same side, respectively, of the test object 16 as the ultrasonic-wave-inducing laser beam 13. The system is characterized by non-contact with the test object by the ultrasonic-wave generation-and-detection means.

14 Claims, 5 Drawing Figures

CONTACT-FREE ULTRASONIC TRANSDUCTION FOR FLAW AND ACOUSTIC DISCONTINUITY DETECTION

BACKGROUND OF THE INVENTION

1. Field of the Invention

This invention relates to ultrasonic transduction and especially to a method and means for remote, contact-free, ultrasonic, non-destructive examination of test objects for flaws and acoustic discontinuities such as solid-to-gas or liquid-to-solid interface.

2. Description of the Prior Art

X-ray examination of test objects, such as jet and reusable rocket engines, for cracks or other flaws has disadvantages, such as expense, complexity, danger to human health, and inability to detect separations and disbonds perpendicular to the beam. Non-destructive examination can also be accomplished by inducing an ultrasonic wave in the test object by means of a piezoelectric transducer and analyzing the wave after its passage through the test object. However, the ultrasonic transducer must be held against the test specimen by the use of wetting or greasing compounds which means that the test object and transducer must be cleaned after the test. This adds labor, time and expense to the test procedure and sometimes leaves an undesirable residue. Also, the apparatus has to be disassembled if an interior component such as a blade or impeller is to be checked. Other types of examination for flaws require the test object to be cut and examined, so that the object is destroyed and cannot be used thereafter.

OBJECTS OF THE INVENTION

An object of the invention is to examine a test object for flaws by non-destructive testing.

Another object is to acoustically examine a test object by the use of ultrasonic waves which are not induced in the test object by a mechanically attached transducer.

A further object is to eliminate the wetting or greasing of the test object and/or transducer when ultrasonic examinations of test objects are made.

Another object is to provide a flexible cable to be inserted through the engine ports to provide non-destructive testing without engine disassembly.

Other objects, advantages and novel features of the present invention will become apparent from the following detailed description of the invention when considered in conjunction with the accompanying drawing.

SUMMARY OF THE INVENTION

The objects and advantages of the present invention are achieved by inducing the formation of ultrasonic waves in a test object by generating stress zones which launch ultrasonic energy through the test object. The stress is produced by intense laser pulses and preferably by laser pulses from a beam array in which the beam-propagating elements are spaced from each other by a distance equal to one-half the acoustic wavelength. The laser pulse rate is the same as the frequency of the acoustic wave.

The ultrasonic wave, after passing through or reflecting from part or all of the test object, is derived from the test object by means of an electrooptical derivation system which does not physically contact the object. Thus, both the induction and derivation systems are contact-free and non-destructive of the test object.

BRIEF DESCRIPTION OF THE DRAWINGS

The same elements or parts throughout the figures of the drawing are designated by the same reference characters, while equivalent elements bear a prime designation.

DETAILED DESCRIPTION OF THE PREFERRED EMBODIMENTS

Figure 1:
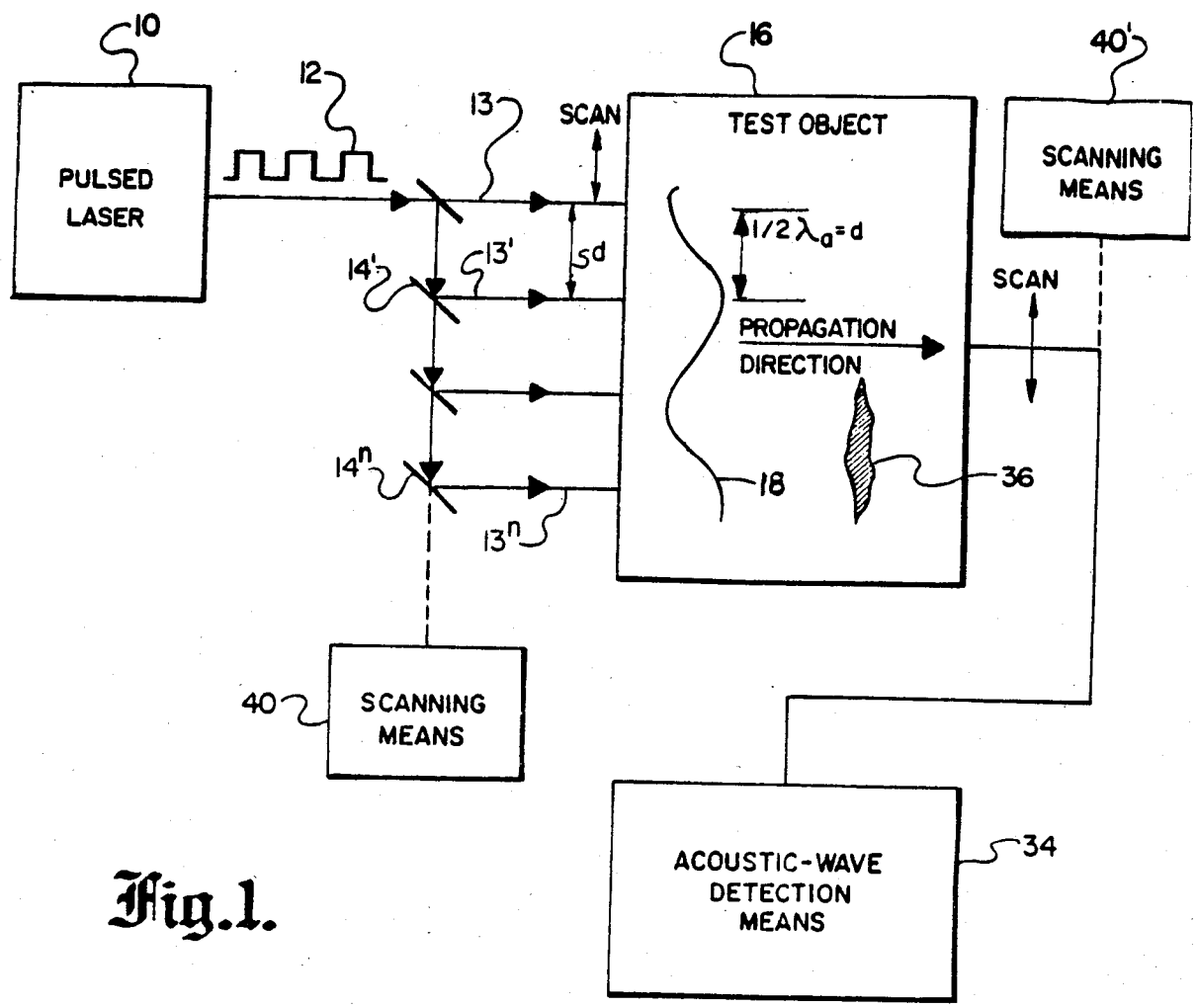
FIG. 1 is a schematic block diagram of an embodiment of the invention.

FIG. 1 shows the manner in which an ultrasonic wave 18 may be induced to propagate in a test object 16, for example, a turbine blade of a jet engine. The localized heating induced in the test object 16 by the intense laser pulses creates thermoelastic waves by photon-phonon interactions. The ultrasonic wave 18 may be induced by direct impingement of a single, pulsed laser beam 12 from a spaced laser source 10 or, preferably, a series of parallel spaced laser beams may be employed. Thus, FIG. 1 shows a plurality of partially reflective, partially transmissive mirrors $14-14^n$ set up to provide parallel beams $13-13^n$ from an incoming, intense, pulsed laser beam 12 which is the output of a pulsed laser source 10. The mirrors $14-14^n$ are spaced from each other by a distance (d) which is preferably equal to one-half the wavelength ($\lambda_a$) of the ultrasonic wave 18 induced in the test object 16, i.e., $d=\frac{1}{2}\lambda$. This spacing allows the beam 13 from each succeeding mirror 14 to reinforce the ultrasonic wave 18 or, in other words, to maintain the ultrasonic wave at constant amplitude. This can be accomplished by maintaining the intensity of each impinging beam $13-13^n$ equal to that of the other beams. The optimum number of mirrors 14 should be about 5 to 10 although, of course, fewer or more could be used. It is apparent that, at ultrasonic frequencies, $\lambda$ would be quite small so the entire extent (vertical in FIG. 1) of the array would be quite small relative to test-object size, perhaps 0.5 mil long.

Figure 2:
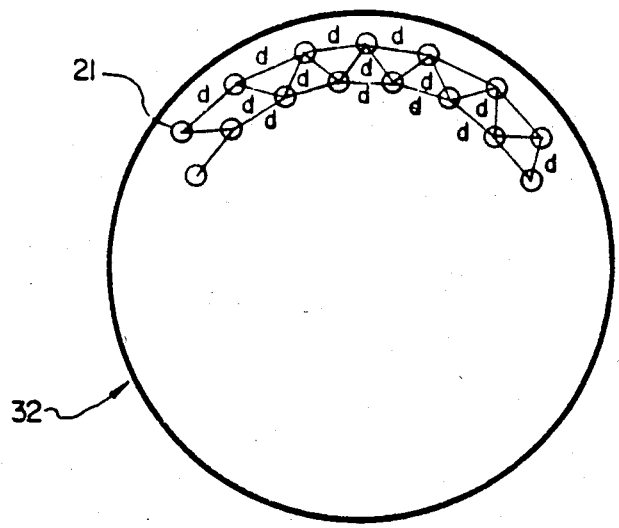
FIG. 2 is a schematic illustration of a bundle of optic fibers and their spacing from each other.

A second, and preferred, type of source of parallel laser beams is a bundle 32 of optical fibers separated from each other by the distance (d)(see FIG. 2). In this case, the output beam from each fiber 21 would have the same energy. The diameter of the bundle 32 might be of the order of 1/16 to $\frac{1}{8}$ inch.

Figure 3:
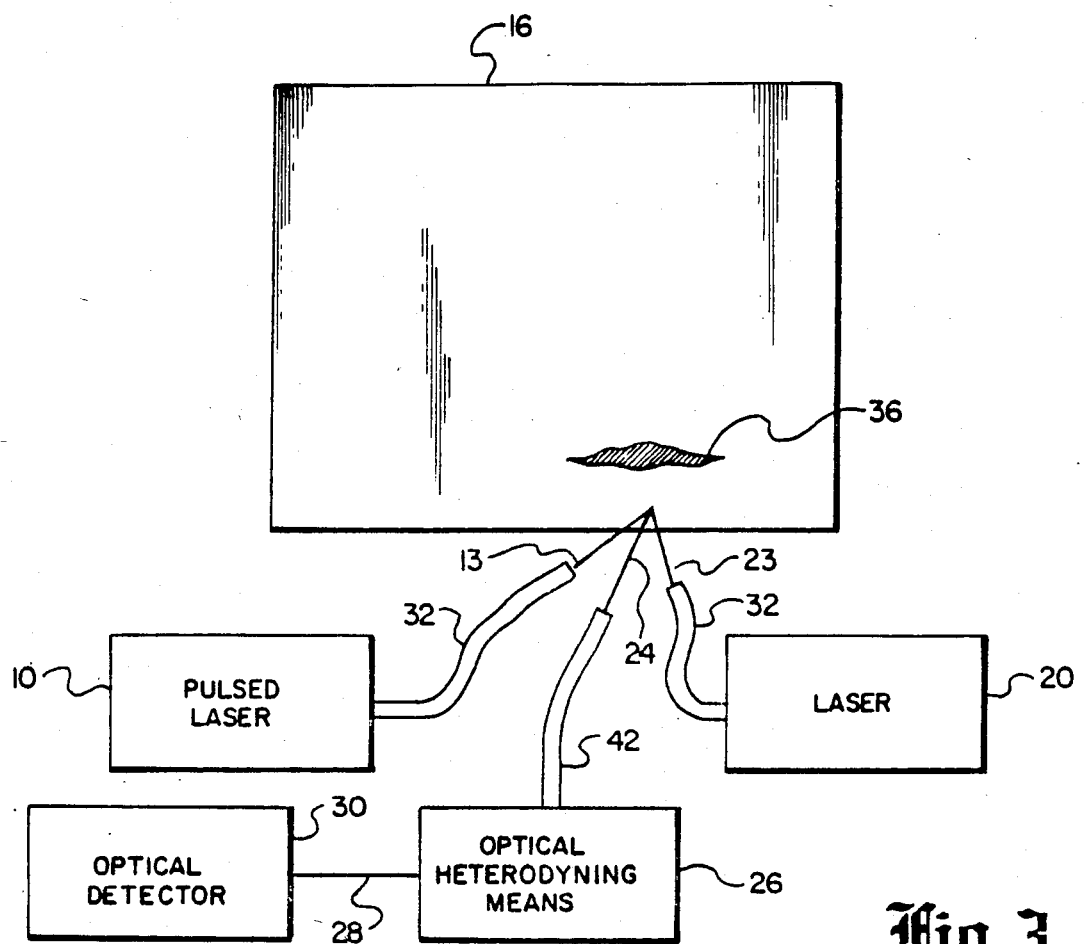
FIG. 3 is a schematic illustration of a system for detecting the ultrasonic waves set up in the test object.

The ultrasonic waves 18 are derived from the test object 16 by means of a suitable detection scheme, indicated generally by the ultrasonic-wave detection means 34. A preferred, contact-free means is shown in FIG. 3.

Figure 4:
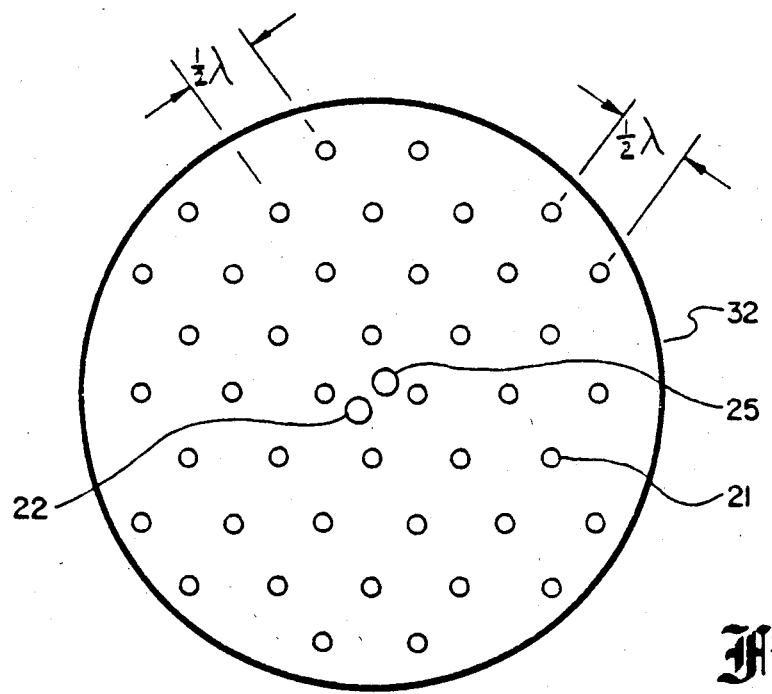
FIG. 4 is a cross-sectional illustration of a fiber bundle which can be employed both for propagation and reception of laser beams.
Figure 5:
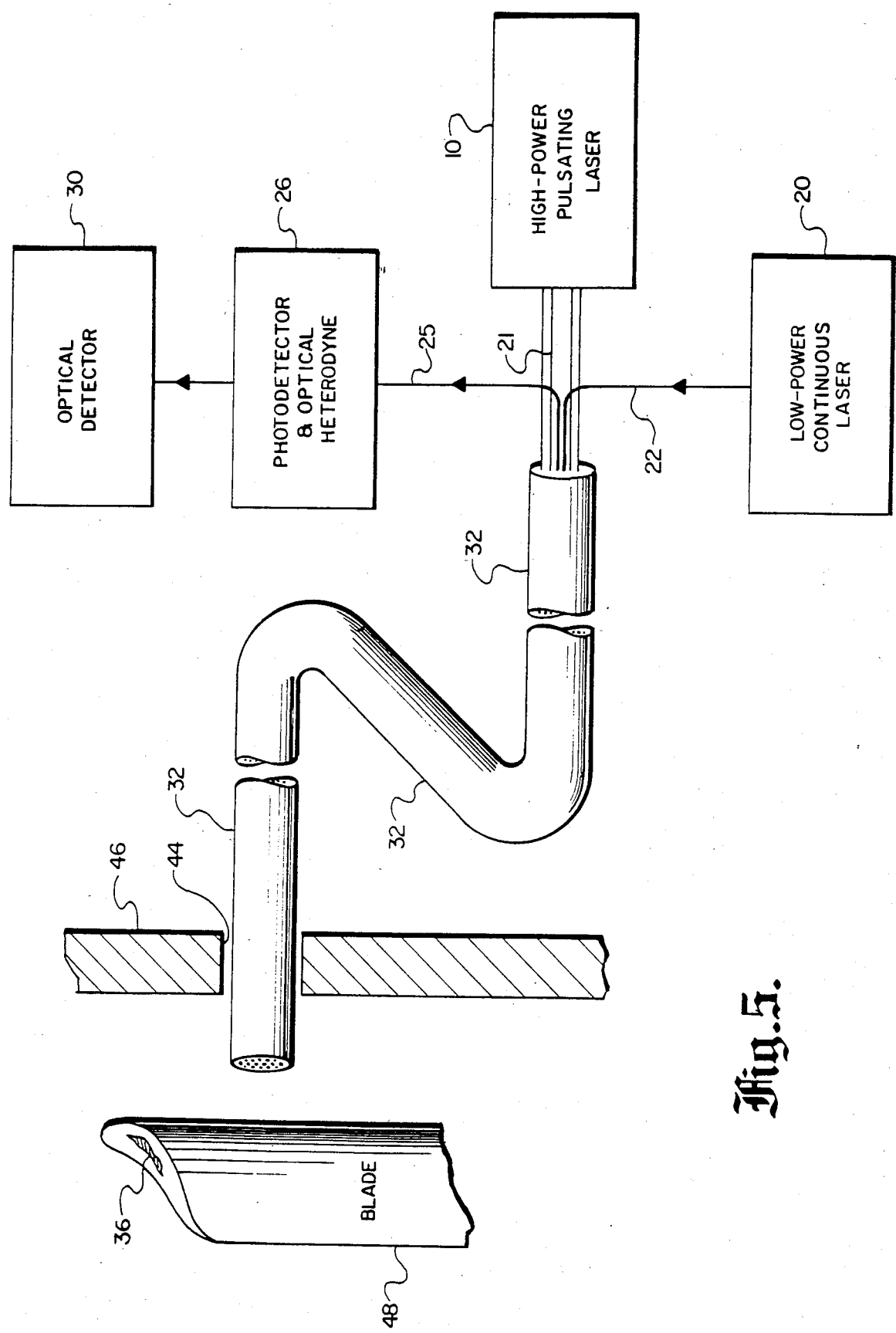
FIG. 5 is a schematic illustration of a flaw-detection system utilizing a single fiberoptic cable threaded through a hole in an engine housing for examining a turbine blade inside the housing.

The ultrasonic waves 18 can be detected by directing a second laser beam, a detection laser beam, preferably continuous rather than pulsed, from a laser source 20 through an optical fiber 22, or group of fibers, 22 onto the test object 16. The second laser beam 23 is preferably aligned with the first laser beams $13-13^n$ if they are on opposite sides of the test object 16 as in FIG. 1, or is aimed to hit the same spot as do the beams from the first pulsed laser 10 if both laser beams are on the same side of the test object as in FIG. 3. In both modes, the laser beams may be somewhat non-coincident, although the preferred method of operation is with coincident beams. The reflected beam 24 is a modulated beam, that is, the frequency, Fo, of the laser 20 is modulated by the frequency, Fa, of the ultrasonic wave 18 and contains a frequency Fo+Fa. The reflected optical beam 24 may be received by a bundle 42 of optical fibers and fed to an optical heterodyning means 26 which separates the laser frequency, Fo, and passes a beam 28 having the ultrasonic frequency, Fa, to an optical detector 30. The optical detector 30 may be a photodetector, for example, which indicates the amplitude of the ultrasonic-frequency beam. The fiber optics in this system could be a bundle 32 of fibers as shown in FIG. 4, in which one or more central fibers 22 and 25 are employed for, respectively, transmitting the detection laser beam and receiving detection laser beam and a group of fibers 21, spaced a distance of λ/2 from each other, surround the detection-system fibers 22 and 25 and are used to propagate the ultrasonic-wave-inducing laser beam. FIG. 5 shows how the fiberoptic cable 32 connects with the lasers 10 and 20 and the detection equipment. The cable 32 can be brought through a hole 44 in an engine housing 46, for example, to scan a turbine blade 48 for flaws.

It should be noted that both the ultrasonic-wave-inducing input-beam means, e.g., the fibers 21, and the detection-system input-beam means, e.g., the optical fiber 22, are scanned simultaneously along the test object 16. They can be placed on opposite sides of the test object 16 and, if a flaw 36 (or acoustic discontinuities such as liquid-to-solid or solid-to-gas interfaces) in the object 16 is encountered in this mode (transmissive mode), the output signal from the optical detector 30 is reduced, since in the transmissive mode, a flaw (or acoustic discontinuities such as liquid-to-solid or solid-to-gas interfaces) reduces the amplitude of the ultrasonic wave 18.

Scanning means are well known and could be either mechanical or electrical, e.g. Bragg cells, through which the beams 13 and 23 pass before impinging on the test object 16. Variation of the voltage applied to each Bragg cell would move the direction of the beam leaving the cell. The beams could also be scanned by mechanical means 40,40' to which the mirrors 14–14ⁿ or the optical-fiber bundles 32 are attached.

The detection-system input beam 23 may be on the same side of the test object 16, as shown in FIG. 3, the laser beams being directed at closely spaced spots and also being scanned together. In this mode of operation (reflective mode) the reflected signal from a flaw 36 (or acoustic discontinuities such as liquid-to-solid or solid-to-gas interfaces) would increase the signal ordinarily reflected from the test object 16 and the output of the optical detector 30 would increase in the presence of a flaw 36.

Thus, a novel optical/ultrasonic system for the detection of flaws and acoustic discontinuities such as liquid-to-solid or solid-to-gas interfaces in test objects has been described herein, which system does not require transducers to be coupled in physical contact with the test object, thus avoiding the problems inherent in the coupling of the transducers to the test object, such as wetting, grease coatings, cleaning, undesirable residues, and others.

Obviously, many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. Apparatus for inducing an ultrasonic wave in a test object, comprising:
    laser pulse means for providing a series of laser pulses; and,
    a plurality of spaced, partially transmissive, partially reflective mirrors arranged to transmit and reflect the output of said laser pulse means,
    wherein, the beam reflected from said mirrors are a plurality of spaced parallel laser beams said beams being directed to impinge on said test object, each beam being spaced from its neighboring beam a distance equal to one-half the wavelength of said ultrasonic wave.

2. Apparatus as in claim 1, wherein;
    the transmittivity-reflectivity ratios of said mirrors are such that each directs an equal amount of energy upon said test object in order to maintain the amplitude of the acoustic wave at a constant level.

3. Apparatus as in claim 1, wherein:
    the number of mirrors is in the range of 5 to 10.

4. Apparatus for inducing an ultrasonic wave in a test object, comprising:
    laser-pulse-generating means for providing a series of laser pulses; and
    fiber optic means for directing the output of said laser-pulse-generating means upon said test object, said fiber optic means comprising a bundle of optical fibers each spaced from its neighbor a distance equal to one-half of the wavelength of said ultrasonic wave,
    wherein, the output from said fiber optic means is a plurality of spaced parallel laser beams, each beam being spaced from its neighboring beam a distance equal to one-half the wavelength of said ultrasonic wave.

5. A system for detecting flaws and acoustic discontinuities such as solid-to-liquid or solid-to-gas interfaces in test objects which is capable of sustaining the generation and propagation of ultrasonic waves comprising:
    light means for inducing ultrasonic waves in said test object, said light means being coupling-free of said test object said light means providing a plurality of spaced parallel light beams directed to impinge on said test object, each beam being spaced from its neighboring beam a distance equal to one-half the wavelength of said ultrasonic wave; and
    light means for detecting said ultrasonic waves in said test object, said detection means being coupling-free of said test object.

6. A flaw-detection or acoustic-discontinuity-detection system as in claim 5, wherein:
    said light beams are laser pulses.

7. A flaw-detection or acoustic-discontinuity-detection system as in claim 6, wherein said light means comprises:
    a plurality of spaced partially transmissive, partially reflective mirrors arranged to transmit and reflect said laser pulses.

8. A flaw-detection or acoustic-discontinuity-detection system as in claim 7, wherein:

the transmittivity-reflectivity ratios of said mirrors are such that each directs sufficient energy upon said test object to compensate for the energy loss which occured during the travel time of the preceding wavelength of the ultrasonic wave.

9. A flaw-detection or acoustic-discontinuity-detection system as in claim 7, wherein:
the number of mirrors is in the range of 5 to 10.

10. A flaw-detection or acoustic-discontinuity-detection system as in claim 6, wherein said detection means comprises:
laser-beam-generating means;
second means for propagating and directing the laser beam from said laser-beam-generating means upon a spot on said test object at which the laser beam frequency can be modulated by the frequency of said ultrasonic wave.

11. A flaw-detection or acoustic-discontinuity-detection system as in claim 10, further including:
optical heterodyning means to which the modulated laser beam is fed for separating out the ultrasonic wave component from the modulated laser beam.

12. A flaw-detection or acoustic-discontinuity-detection system as in claim 11, wherein:
the two laser beams which are directed upon said test object are made to scan the test object in synchronism.

13. A flaw-detection or acoustic-discontinuity-detection system as in claim 11, further including:
an optical detector connected to said optical heterodyning means for producing an output signal from the ultrasonic wave component, the amplitude of the output signal varying when flaws in the test object are encountered by the ultrasonic wave.

14. A system for directing flaws and acoustic discontinuities such as solid-to-liquid or solid-to-gas interfaces in test objects which are capable of sustaining the generation and propagation of ultrasonic waves comprising:
fiber optic means for inducing ultrasonic waves in said test object, said induction means being coupling-free of said test object, said fiber optic means comprising a bundle of optical fibers each spaced from its neighbor a distance equal to one-half the wavelength of said ultrasonic wave; and,
light means for detecting said ultrasonic waves in said test object, said detection means being coupling-free of said test object.

* * * * *